United States Patent
Kobayashi (10) Patent No.: US 9,618,473 B2
(45) Date of Patent: Apr. 11, 2017

(54) GAS SENSOR

(75) Inventor: Kiyomi Kobayashi, Kuwana (JP)

(73) Assignee: DENSO CORPORATION, Kariya (JP)

( * ) Notice: Subject to any disclaimer, the term of this patent is extended or adjusted under 35 U.S.C. 154(b) by 328 days.

(21) Appl. No.: 13/490,687

(22) Filed: Jun. 7, 2012

(65) Prior Publication Data

US 2012/0312685 A1 Dec. 13, 2012

(30) Foreign Application Priority Data

Jun. 9, 2011 (JP) ................................. 2011-129214
Jan. 6, 2012 (JP) ................................. 2012-001028

(51) Int. Cl.
G01N 27/407 (2006.01)

(52) U.S. Cl.
CPC ................................. *G01N 27/4078* (2013.01)

(58) Field of Classification Search
CPC ........................................ G01N 27/407–27/41
USPC ...................... 204/424–429; 205/783.5–785; 73/23.31–23.32
See application file for complete search history.

(56) References Cited

U.S. PATENT DOCUMENTS

| 4,328,294 A * | 5/1982 | Tanaka et al. ................ 429/304 |
| 2001/0023611 A1* | 9/2001 | Matsuo et al. ................ 73/31.05 |
| 2003/0116435 A1* | 6/2003 | Satou et al. ................... 204/424 |
| 2005/0241368 A1 | 11/2005 | Yamauchi et al. |
| 2008/0314117 A1* | 12/2008 | Sato et al. ...................... 73/23.32 |
| 2011/0017596 A1* | 1/2011 | Kamiya et al. ................ 204/424 |

FOREIGN PATENT DOCUMENTS

| JP | 2003-114210 | 4/2003 |
| JP | 2005-326394 | 11/2005 |
| WO | WO 2009125666 A1 * | 10/2009 |

OTHER PUBLICATIONS

Office Action (2 pages) dated May 7, 2013, issued in corresponding Japanese Application No. 2012-001028 and English translation (2 pages).

* cited by examiner

*Primary Examiner* — Luan Van
*Assistant Examiner* — Maris R Kessel
(74) *Attorney, Agent, or Firm* — Nixon & Vanderhye P.C.

(57) ABSTRACT

A gas sensor has a cylindrical housing case, a gas sensor element as a sensor component, and a filler portion. The filler portion is formed between the inner surface of the cylindrical housing case and the outer surface of the gas sensor element. The filler portion is filled with filler powder composed of talc as a layered compound. Talc is a principal ingredient of the filler powder. The space formed between the cylindrical housing case and the gas sensor element is sealed with the filler powder in the filler portion. The filler powder in the filler portion has a degree of c-axis orientation within a range of 60% to 85%, The filler powder in the filler portion has a porosity of not more than 10%.

8 Claims, 7 Drawing Sheets

GAS SENSOR

CROSS-REFERENCE TO RELATED APPLICATION

This application is related to and claims priority from Japanese Patent Applications No. 2011-129214 filed on Jun. 9, 2011, and No. 2012-001028 filed on Jan. 6, 2012, the contents of which are hereby incorporated by reference.

BACKGROUND OF THE INVENTION

1. Field of the Invention

The present invention relates to gas sensors for detecting a concentration of a specified gas component contained in a detection target gas such as exhaust gas emitted from an internal combustion engine.

2. Description of the Related Art

In general, one or more gas sensors are installed in an exhaust gas system mounted to a motor vehicle in order to detect a concentration of a specified gas component such as oxygen gas contained in exhaust gas emitted from an internal combustion engine of a motor vehicle.

Such a gas sensor has a structure in which a gas sensor element is fixed in the inside of a cylindrical housing case. Such a gas sensor has another structure in which an insulator is fixed in the inside of the cylindrical housing case, and a gas sensor element is fixed in the inside of the insulator.

For example, a conventional patent document, Japanese patent laid open publication No. JP 2003-114210, discloses a structure of a conventional gas sensor having a filler portion which is formed between the cylindrical housing case and another component of the gas sensor, specifically, formed between the housing case and the gas sensor element or between the housing case and the insulator. Granulated powder of talc (or talcum powder) is used as such filler powder. Using such filler powder makes it possible to provide a necessary airtightness between the housing case and the gas sensor element or the insulator in order to separate a detection target gas (exhaust gas) from a reference gas (for example, the atmosphere).

However, a temperature of exhaust gas is more increased due to increasingly strict vehicle emission regulations. This often causes a problem, namely, decreases the airtightness in the space formed between the housing case and the gas sensor element or the insulator in the conventional gas sensor having the structure previously described. If the airtightness of the gas sensor is decreased, an output of the gas sensor is decreased. As a result, the gas sensor becomes inaccurate.

Figure 7A:
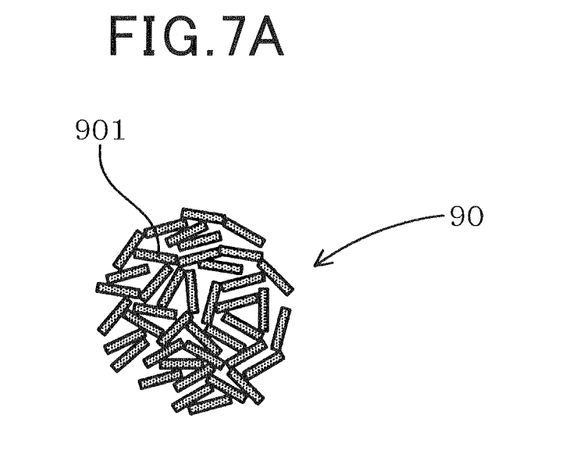
FIG. 7A is an explanation view showing granulated powder composed of talc used in a conventional gas sensor.
Figure 7B:
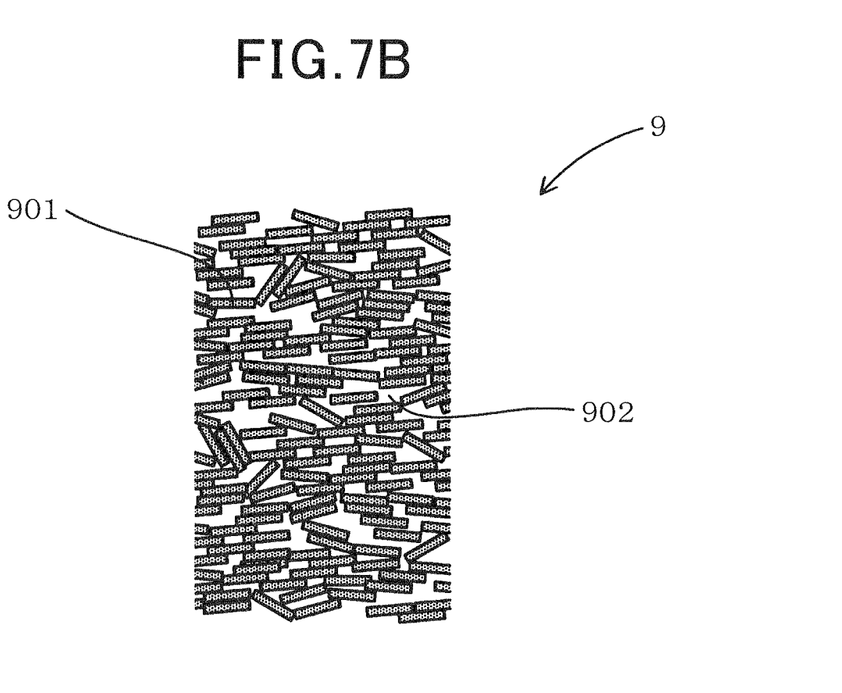
FIG. 7B is an explanation view showing a structure of a filler portion of the conventional gas sensor which is filled with granulated powder composed of thin-leaf shaped grains of talc.

FIG. 7A is a view showing conventional granulated powder 90 composed of talc 901 having a thin-leaf shape (or a scale shape). FIG. 7B is a view showing a structure of a filler portion which is filled with granulated powder 90 composed of thin-leaf shaped grains of talc 901.

The inventors according to the present invention investigated and studied the following matters which cause the deterioration of the airtightness of the gas sensor. When the space or gap between the housing case and the gas sensor element or between the housing case and the insulator in the conventional gas sensor is filled with the granulated powder 90 by applying a predetermined pressure, the filler portion 9 composed of the talc has a high degree of orientation of not less than 90% as shown in FIG. 7B because the thin-leaf shaped grains of talc 901 slide relative to each other.

The filler portion 9 which is filled with talc of a high degree of orientation has a very small coefficient of thermal expansion in a radial direction of the gas sensor (which is perpendicular to an axial direction of the gas sensor element in which the gas sensor element or the insulator is inserted into the cylindrical housing case).

The conventional gas sensor having the filler portion 9 cannot adequately follow the repetition of thermal shock cycle test of expansion and contraction of each of the housing case, the gas sensor element, the insulator, etc. This deteriorates the airtightness of the filler portion 9 in the conventional gas sensor.

Further, voids 902 and gaps are generated in the filler portion 9 composed of the granulated powder 90 in the conventional gas sensor by the repetition of thermal test cycle of executing expansion and contraction. This makes the thin-leaf shaped grains of talc 901 in the filler portion 9 in the conventional gas sensor move easily when a force is applied to the conventional gas sensor in a direction which is different from an axial direction of the conventional gas sensor. As a result, this decreases the airtightness of the filler portion 9 in the conventional gas sensor.

SUMMARY

It is therefore desired to provide a gas sensor capable of better preventing the airtightness of a filler portion formed between a cylindrical housing case and a gas sensor element from being decreased.

An exemplary embodiment provides a gas sensor having a cylindrical housing case, a gas sensor element and a filler portion. The gas sensor element is fixed in the inside of the cylindrical housing case. The filler portion is formed between the inner surface of the cylindrical housing case and the outer surface of a sensor component installed in the inside of the gas sensor. For example, the filler portion is formed between the inner surface of the cylindrical housing case and the outer surface of the gas sensor element which is the sensor component. The filler portion is filled with filler powder. The filler powder is composed of talc as a principal ingredient thereof. The talc is a layered compound. The filler portion formed between the cylindrical housing case and the sensor component is sealed with the filler powder. In the gas sensor, the talc in the filler powder has a degree of c-axis orientation within a range of 60% to 85%. Further, the porosity of the filler portion is not more than 10%.

The gas sensor according to the exemplary embodiment of the present invention has the degree of c-axis orientation of talc within a range of 60% to 85%. The filler portion has a porosity of not more than 10%. This structure of the gas sensor makes it possible to adapt the filler portion to a repetition of expansion and contraction of each of components such as the housing case, the gas sensor element, an insulator, etc., in the gas sensor. This improved feature of the gas sensor makes it possible to better prevent the airtightness of the filler portion from being deteriorated, namely, decreased. Even if a force is applied along a direction which is different from an axial direction of the gas sensor, the filler powder in the filler portion made of talc, as the principal ingredient thereof, is difficult to move. This makes it also possible to better prevent the airtightness of the filler portion from being deteriorated. The degree of c-axis orientation of talc as previously described shows a ratio of arranging the c-axis of talc along an axial direction of the gas sensor.

The improved structure of the gas sensor according to the exemplary embodiment of the present invention makes it possible to better prevent the airtightness of the filler portion formed between the housing case and the sensor element such as the gas sensor element and an insulator from being deteriorated.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Hereinafter, various embodiments of the present invention will be described with reference to the accompanying drawings. In the following description of the various embodiments, like reference characters or numerals designate like or equivalent component parts throughout the several diagrams.

A description will be given of a gas sensor according to the present invention. The gas sensor according to the present invention has a cylindrical housing case, a gas sensor element and a filler portion. The gas sensor element is fixed in the inside of the cylindrical housing case. The filler portion is formed between the inner surface of the cylindrical housing case and the outer surface of a sensor component installed in the inside of the gas sensor. The filler portion is filled with filler powder. The filler powder is composed of compressed powder of talc made from natural mineral. In particular, the talc in the filler portion has a degree of c-axis orientation of talc within a range of 60% to 85%.

When the degree of c-axis orientation of talc in the filler portion exceeds the above range, namely, more than 85%, filler powder moves easily in the filler portion by fluctuation of a direction of force applied along an axial direction of the gas sensor when a motor vehicle is running and an exhaust gas system equipped with the gas sensor is vibrated. In this case, when a temperature of the exhaust gas system is increased, a difference in thermal expansion between the filler portion and the cylindrical housing case increases. This easily decreases the airtightness of the filler portion in the gas sensor.

On the other hand, when the degree of c-axis orientation of talc in the filler portion is less than the above range, namely, is less than 60%, the number or amount of talc having a thin-leaf shape (or scale shape), which is arranged approximately in parallel to an axial direction of the gas sensor, is increased. This makes it possible to easily diffuse gas along an axial direction of the gas sensor. As a result, the degree of airtightness of the filler portion is decreased. Accordingly, it is preferable for the talc in the filler portion of the gas sensor to have the degree of c-axis orientation of talc within the range of 65% to 80%.

Figure 5:
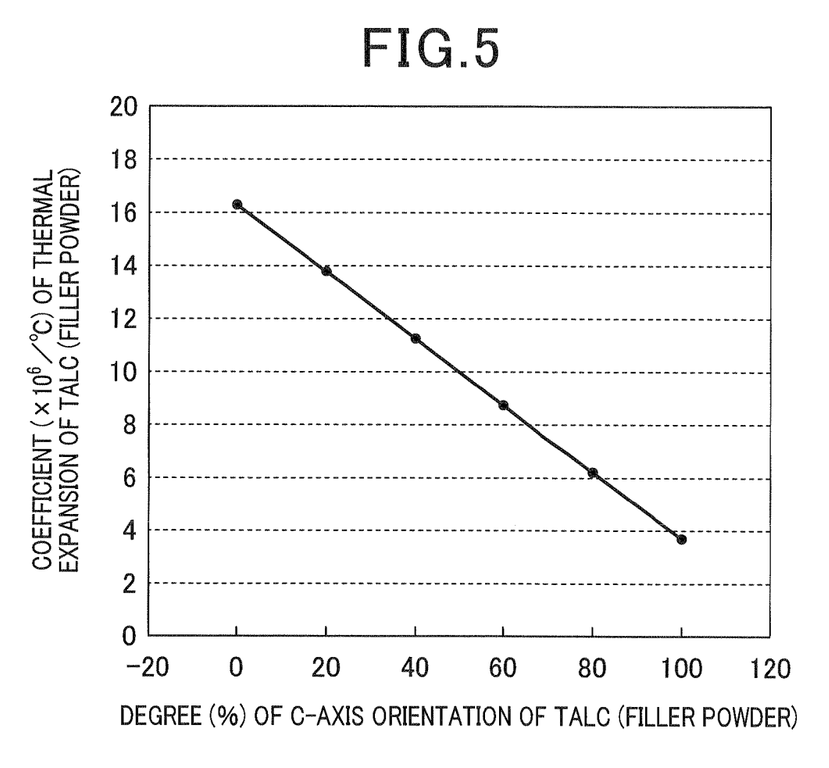
FIG. 5 shows a graph of a relationship between a coefficient of thermal expansion (CTE) and a degree of c-axis orientation of talc used in the filler portion of the gas sensor according to the first exemplary embodiment of the present invention.

FIG. 5 shows a graph which indicates a relationship between a coefficient of thermal expansion (CTE) and a degree of c-axis orientation of talc used in the filler portion of the gas sensor.

It is possible to detect the degree of c-axis orientation of talc as filler powder on the basis of the coefficient of thermal expansion (CTE) of the talc. That is, as shown in FIG. 5, there is a relationship between the filler powder composed of talc and the coefficient of thermal expansion (CTE) of the filler powder. As a result, it is possible to detect the degree of c-axis orientation of talc on the basis of the detected coefficient of thermal expansion of the filler powder. A detailed method of detecting the coefficient of thermal expansion (CTE) of talc in the filler portion will be explained later.

The filler powder in the filler portion formed in the gas sensor according to the present invention has a porosity of not more than 10%.

When the porosity of the filler powder in the filler portion exceeds 10%, filler powder moves easily in the filler portion by fluctuation of a direction of force applied along an axial direction of the gas sensor when a motor vehicle is running and an exhaust gas system equipped with the gas sensor is vibrated. Accordingly, it is preferable for the filler powder in the filler portion formed in the gas sensor to have the porosity not more than 8%, and more preferable to have the porosity of not more than 7.5%.

For example, a mercury press-in method can detect the porosity of the filler portion in the gas sensor. A concrete example of the mercury press-in method capable of detecting the porosity of the filler portion in the gas sensor will be explained later.

In the structure of the gas sensor according to the present invention, the filler portion is formed between the cylindrical housing case and the gas sensor element. The space or gap between the cylindrical housing case and the gas sensor element is filled with the filler powder and sealed by the filler portion.

It is possible to form the cylindrical housing case with a metal which has a coefficient of thermal expansion within a range of $10\times10^{-6}/°$ C. to $12\times10^{-6}/°$ C. There are sensor components in the gas sensor such as the gas sensor element, an insulator, etc. It is possible for each of the sensor components to have a coefficient of thermal expansion within a range of $7\times10^{-6}/°$ C. to $11\times10^{-6}/°$ C.

It is possible for the gas sensor according to the present invention to have a structure in which the filler portion is formed between the cylindrical housing case and the gas sensor element. The gas sensor element is one of the sensor components of the gas sensor.

This structure of the gas sensor makes it possible to have the filler portion having a coefficient of thermal expansion (CTE) in a diameter direction of the filler portion which is close to the coefficient of thermal expansion (CTE) of the cylindrical housing case and the gas sensor element, where the filler portion is filled with filler powder having a degree of c-axis orientation within a range of 60% to 85% and a porosity of not more than 10%. Accordingly, the filler portion in the gas sensor can easily handle a repetition of thermal shock cycle of expansion and contraction of the cylindrical housing case and the gas sensor element. This makes it possible to keep the airtightness of the filler portion formed between the cylindrical housing case and the gas sensor element, and to more better prevent the airtightness of the filler portion from being deteriorated.

For example, there is a gas sensor equipped with a cup shaped gas sensor element (or a cup type gas sensor) as a concrete gas sensor having a structure in which the filler portion is formed between the cylindrical housing case and the gas sensor element.

It is possible for the gas sensor according to the present invention to have a structure in which an insulator is installed in the inside of the cylindrical housing case, and the gas sensor element is installed in the inside of the insulator. In this structure of the gas sensor, the insulator is one of the sensor components, and the filler portion is formed between the cylindrical housing case and the insulator.

This structure of the gas sensor makes it possible to have the filler portion having a coefficient of thermal expansion (CTE) in a diameter direction of the filler portion which is close to the coefficient of thermal expansion (CTE) of the cylindrical housing case and the insulator, where the filler portion is filled with filler powder having the degree of c-axis orientation within the range of 60% to 85% and the porosity of not more than 10%. Accordingly, the filler portion in the gas sensor can easily handle a repetition of thermal shock cycle of expansion and contraction of the cylindrical housing case and the insulator caused. This makes it possible to keep the airtightness of the filler portion, and to more better prevent the airtightness of the filler portion formed between the cylindrical housing case and the insulator from being deteriorated.

For example, there is a gas sensor equipped with a lamination type gas sensor element as a concrete gas sensor having a structure in which the filler portion is formed between the cylindrical housing case and the insulator.

It is preferable for the gas sensor according to the present invention to have a structure in which the gas sensor element has a solid electrolyte made of zirconia (or zirconium dioxide) or partially stabilized zirconia, and the cylindrical housing case is made of stainless steel. Further, it is preferable that the insulator is made of alumina.

This structure of the gas sensor makes it possible to have the filler portion having a coefficient of thermal expansion in a diameter direction of the filler portion which can be more approached to the coefficient of thermal expansion of the cylindrical housing case, the gas sensor element and the insulator. Accordingly, the filler portion in the gas sensor easily handles a repetition of thermal shock cycle of expansion and contraction of the cylindrical housing case and the gas sensor element or the insulator. This makes it possible to keep the airtightness of the filler portion, and to more better prevent the airtightness of the filler portion formed between the cylindrical housing case and the gas sensor element or the insulator from being deteriorated.

It is preferable for the gas sensor according to the present invention to have a structure in which the filler portion is filled with compressed powder of natural mineral of talc. That is, it is preferable to form the filler portion by putting the compressed powder of pulverized talc, not granulated powder of talc into the filler portion and by pressing the compressed powder in the filler portion.

Figure 4A:
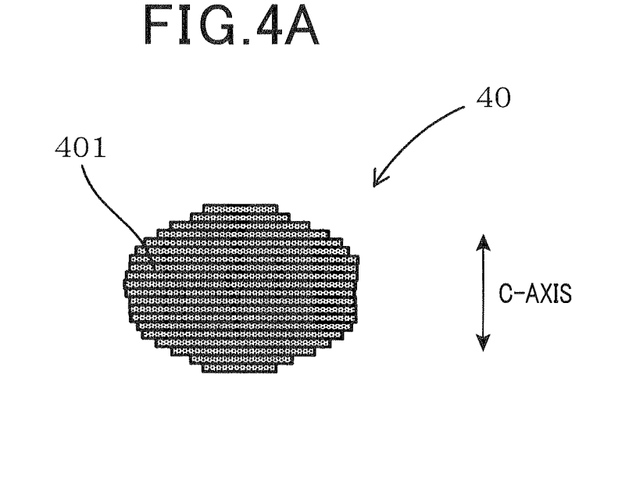
FIG. 4A is an explanation view showing compressed powder made from natural mineral of talc which is used in a filler portion of the gas sensor according to the first exemplary embodiment of the present invention.
Figure 4B:
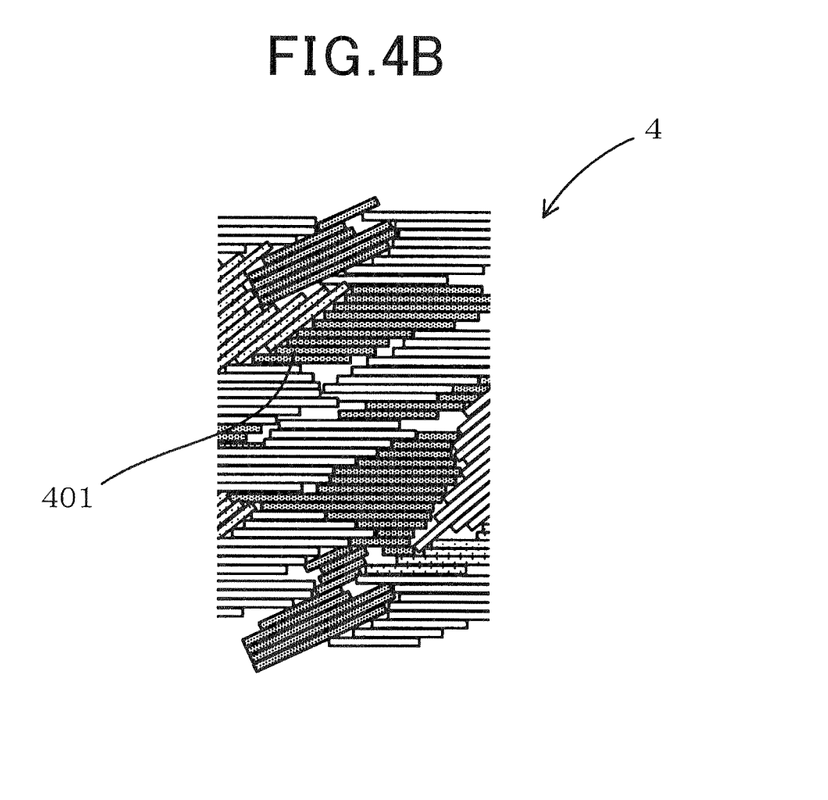
FIG. 4B is an explanation view showing the filler portion of the gas sensor according to the first exemplary embodiment which is filled with the talc shown in FIG. 4A.

FIG. 4A is an explanation view showing compressed powder of natural mineral of talc for use in the filler portion 4 of the gas sensor according to the present invention. FIG. 4B is an explanation view showing the filler portion 4 of the gas sensor, which is filled with the talc shown in FIG. 4A.

In the compressed powder 40 made of natural mineral of talc stored in the filler portion 4, as shown in FIG. 4A, a plurality of thin-leaf shaped grains of talc 401 (or scale talc) is arranged along the same direction and a plurality of the thin-leaf shaped grains of talc 401 (as a layer compound) is laminated. In each compressed powder 40, the thin-leaf shaped grains of talc 401 has the degree of c-axis orientation of approximately 100%)

As shown in FIG. 4B, when a predetermined force is applied to the compressed powder 40 stored in the filler portion 4 of the gas sensor 1, the thin-leaf shaped grains of talc 401 (as a layer compound forming the compressed powder 40) slides relative to each other. The filler portion 4 formed between the cylindrical housing case and the gas sensor element or the insulator is completely filled with the thin-leaf shaped grains of talc 401. The thin-leaf shaped grains of talc 401 forming the compressed powder 40 slides in the same direction. However, as shown in FIG. 4B, each compressed powder 40 is arranged in a different direction in the filler portion 4. Accordingly, a plurality of groups as the compressed powder 40 is generated and each group has a plurality of thin-leaf shaped grains of talc 401 which is arranged in the same direction. The thin-leaf shaped grains of talc 401 in the same group slides in the same direction, but the thin-leaf shaped grains of talc 401 in different groups is arranged in a different direction in the filler portion shown in FIG. 4B. A different hatching in FIG. 4B indicates a different group of the thin-leaf shaped grains of talc 401. As shown in FIG. 4B, a plurality of the thin-leaf shaped grains of talc 401 in one group is arranged in the same direction, but the thin-leaf shaped grains of talc 401 in another group is arranged in a different direction. This makes it possible to easily have the talc having the degree of c-axis orientation within the range of 60% to 85%. The c-axis of talc is the direction along which natural mineral of talc as a layered compound is laminated (see FIG. 4A).

It is preferable for the gas sensor according to the present invention to have a structure in which the compressed powder in the filler portion has an average particle size within a range of 100 μm to 600 μm. This makes it possible to more easily form the filler portion having the degree of c-axis orientation within the range of 60% to 85% and the porosity of not more than 10%.

It is more preferable for the compressed powder in the filler portion to have the average particle size (or an average diameter) within a range of 200 μm to 500 μm (namely, the average particle size of not less than 200 μm and not more than 500 μm).

It is preferable that the filler powder is composed of the compressed powder which is coated with water or inorganic binder. This makes it possible to form the talc in the filler portion to easily slide relative to each other because the talc has the degree of c-axis orientation within the range of 60% to 85% and the porosity of not more than 10%. Using inorganic binder can more decrease the porosity because such inorganic binder remains in the filler portion.

In the gas sensor according to the present invention, it is preferable to add water of not more than 1.5 mass % into compressed powder of 100 mass %. This structure of the gas sensor makes it possible to more easily form the filler portion with the compressed powder having the porosity of not more than 10%.

It is preferable to add inorganic binder of not more than 3 mass % into compressed powder of 100 mass %. This structure of the gas sensor makes it possible to more easily form the filler portion with the inorganic binder having the degree of c-axis orientation of not more than 85%.

It is preferable for the gas sensor according to the present invention to have the filler portion with the compressed powder whose coefficient of thermal expansion is within a range of $5.5 \times 10^{-6}/°$ C. to $8.8 \times 10^{-6}/°$ C. This structure of the gas sensor makes it possible to more increase the airtightness of the filler portion.

There is a gas sensor having the features previously described features which is comprised of a cylindrical housing case, a gas sensor element installed in the cylindrical housing case, and a filler portion. The filler portion seals at least a part between the cylindrical housing case and the gas sensor element. There is a gas sensor equipped with a cup shaped gas sensor element (or a cut type gas sensor element) as a concrete example having the above features.

Further, there is a gas sensor having the features previously described, which is comprised of a cylindrical housing case, an insulator installed in the cylindrical housing case, a gas sensor element installed in the inside of the insulator, and a filler portion. The filler portion seals at least a part between the cylindrical housing case and the insulator. There is a gas sensor equipped with a lamination-type gas sensor element as a concrete example having the above features.

First Exemplary Embodiment

A description will now be given of a gas sensor element according to an exemplary embodiment of the present invention with reference to FIG. 1 to FIG. 5.

Figure 1:
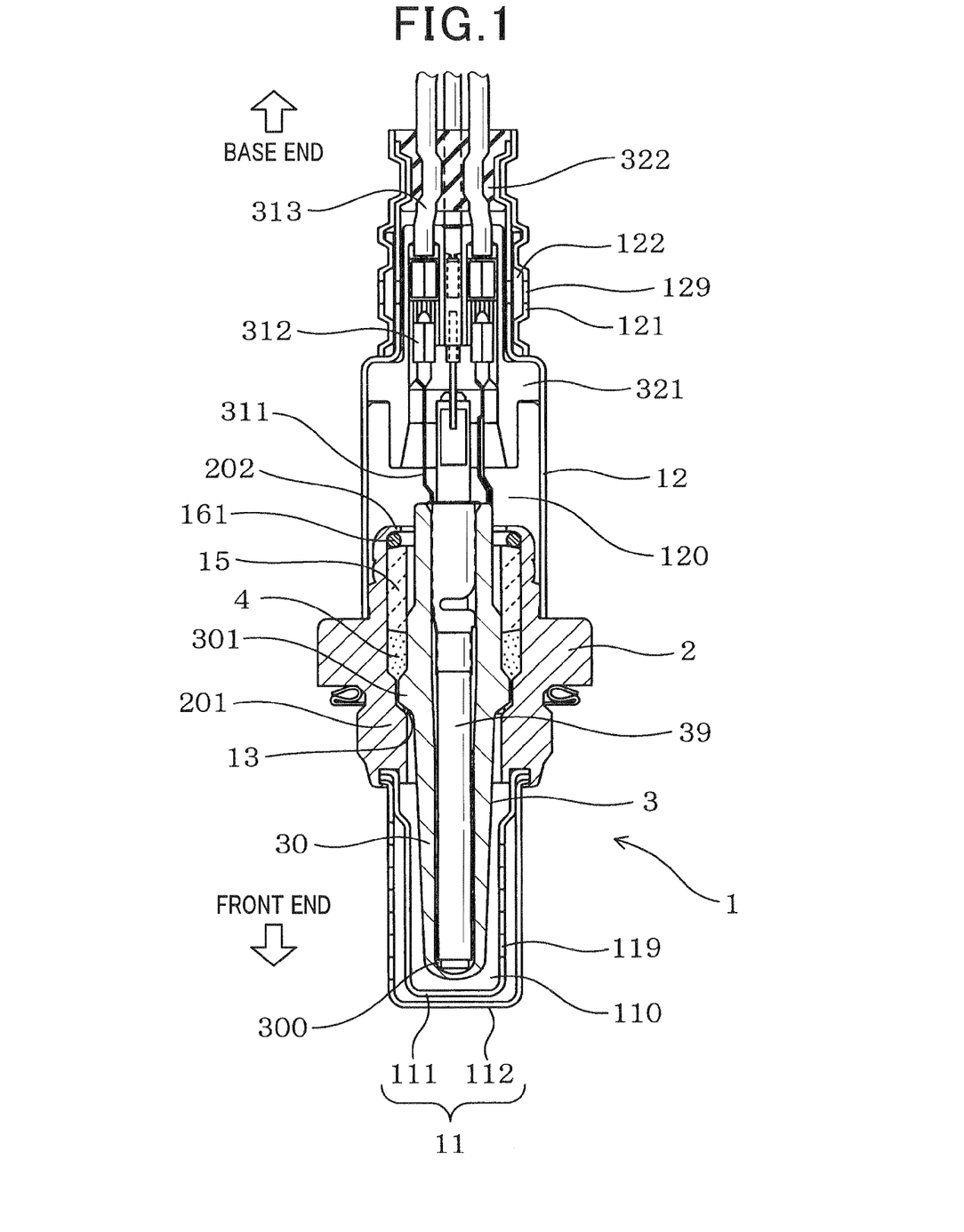
FIG. 1 is a view showing a cross section of a gas sensor equipped with a gas sensor element of a cup shape along a longitudinal direction of the gas sensor according to a first exemplary embodiment of the present invention.
Figure 2:
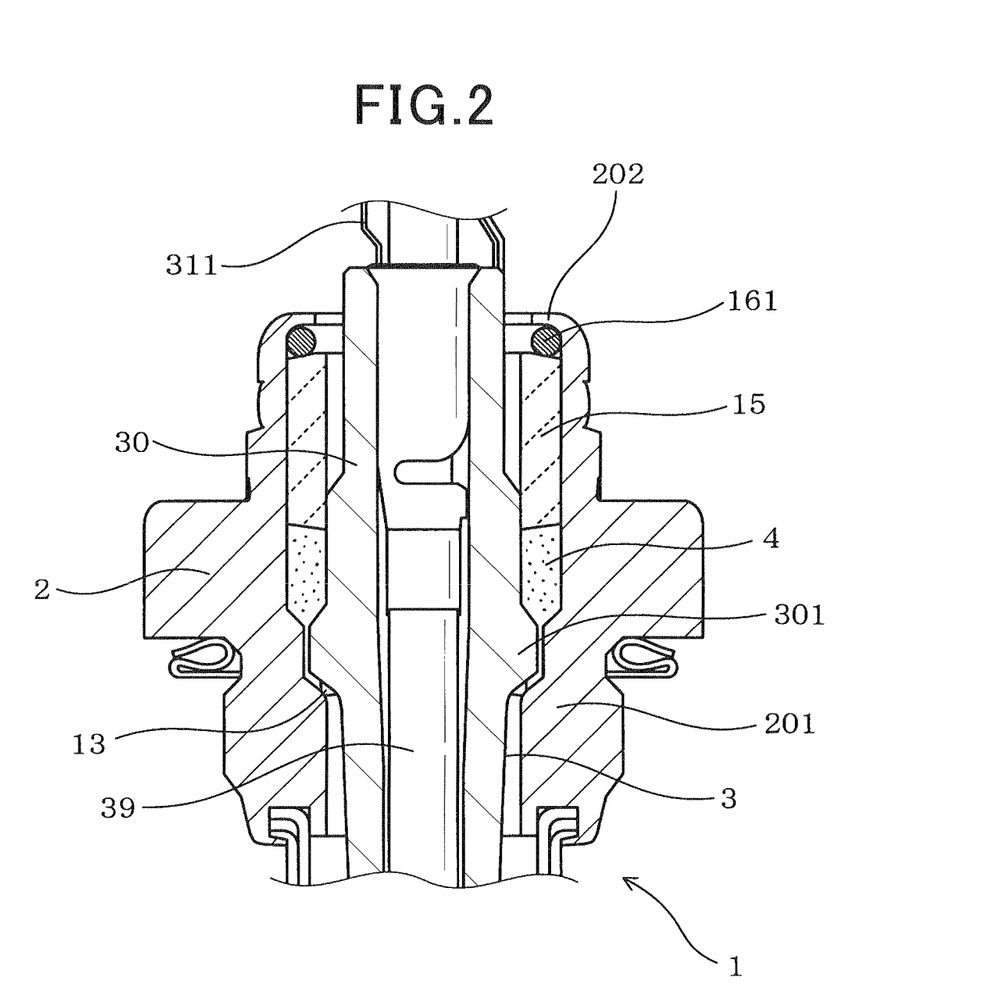
FIG. 2 is an explanation view showing a portion around a cylindrical housing case in the gas sensor according to the first exemplary embodiment of the present invention.

FIG. 1 is a view showing a cross section of the gas sensor 1 along a longitudinal direction of the gas sensor 1 according to the first exemplary embodiment. FIG. 2 is an explanation view showing a portion around a cylindrical housing case 2 in the gas sensor 1 according to the first exemplary embodiment.

As shown in FIG. 1, the gas sensor 1 according to the first exemplary embodiment has the cylindrical housing case 2, a gas sensor element 3 installed in the inside of the cylindrical housing case 2, and a filler portion 4. The filler portion is formed between the cylindrical housing case 2 and the gas sensor element 3 in the gas sensor 1. The filler portion 4 is filled with filler powder composed of talc as a layered compound. That is, a space or gap between the inner surface of the cylindrical housing case 2 and the outer surface of the gas sensor element 3 is filled with talc composed of layered compound, and sealed in order to make the filler portion 4. The first exemplary embodiment uses the gas sensor element 3 as one of sensor components of the gas sensor 1.

A description will now be given of a detailed explanation of the gas sensor 1 according to the first exemplary embodiment.

The gas sensor 1 according to the first exemplary embodiment is an air fuel ratio sensor to be installed in an exhaust gas system of an internal combustion engine mounted to a motor vehicle.

As shown in FIG. 1 and FIG. 2, the cylindrical housing case 2 is made of stainless steel such as Steel Use Stainless (SUS according to Japanese Industrial Standards) which has a coefficient of thermal expansion (CTE) of $11.5 \times 10^{-6}/°$ C. The gas sensor element 3 is inserted in and fixed to the inside of the cylindrical housing case 2. A detection target gas cover 11 is formed at a front end of the cylindrical housing case 2. An atmosphere cover 12 is formed at a base end of the cylindrical housing case 2. Through the description of the specification, the front end of the cylindrical housing case 2 is a side which is inserted into and fixed to an exhaust gas system of an internal combustion engine (not shown). That is, the front end of the cylindrical housing case 2 in the gas sensor 1 is exposed to exhaust gas which flows in an exhaust gas pipe (not shown) of the exhaust gas system. The base end of the cylindrical housing case 2 is a side opposite to the front end of the cylindrical housing case 2.

As shown in FIG. 1, the detection target gas cover 11 has a double structure which is composed of an inner cover 111 and an outer cover 112. Introduction holes 119 are formed in each of the inner cover 111 and the outer cover 112 of the detection target gas cover 11. Exhaust gas, which flows in the exhaust gas pipe (not shown) of an exhaust gas system of an internal combustion engine, is introduced into the inside of the detection target gas cover 11 through the introduction holes 119. This makes a detection target gas in the inside of the detection target gas cover 11 of the cylindrical housing case 2.

An outer cover is installed at the base end of the atmosphere cover 12 through a water repelling filter. Introduction holes 129 are formed in the atmosphere cover 12 and an outside cover 121, which are face to each other through the water repelling filter 122. Atmospheric air is introduced in the inside of the atmosphere cover 12 through the introduction holes 129 in order to provide a reference gas in the gas sensor 1, namely, to provide the atmosphere 120 in the gas sensor 1.

The gas sensor element 3 is composed of a solid electrolyte 30 of a cup shape and a pair of an outside electrode and an inside electrode (omitted from the drawings). The outside electrode is formed at the outside surface of the solid electrolyte 30. The inside electrode is formed in the inside surface of the solid electrolyte 30. An atmosphere chamber 300 is formed in the inside of the solid electrolyte 30. The atmosphere chamber 300 communicates with the atmosphere 120 in the gas sensor 1. The solid electrolyte 30 is made of zirconia having a coefficient of thermal expansion of $8.5 \times 10^{-6}/°$ C.

Figure 3:
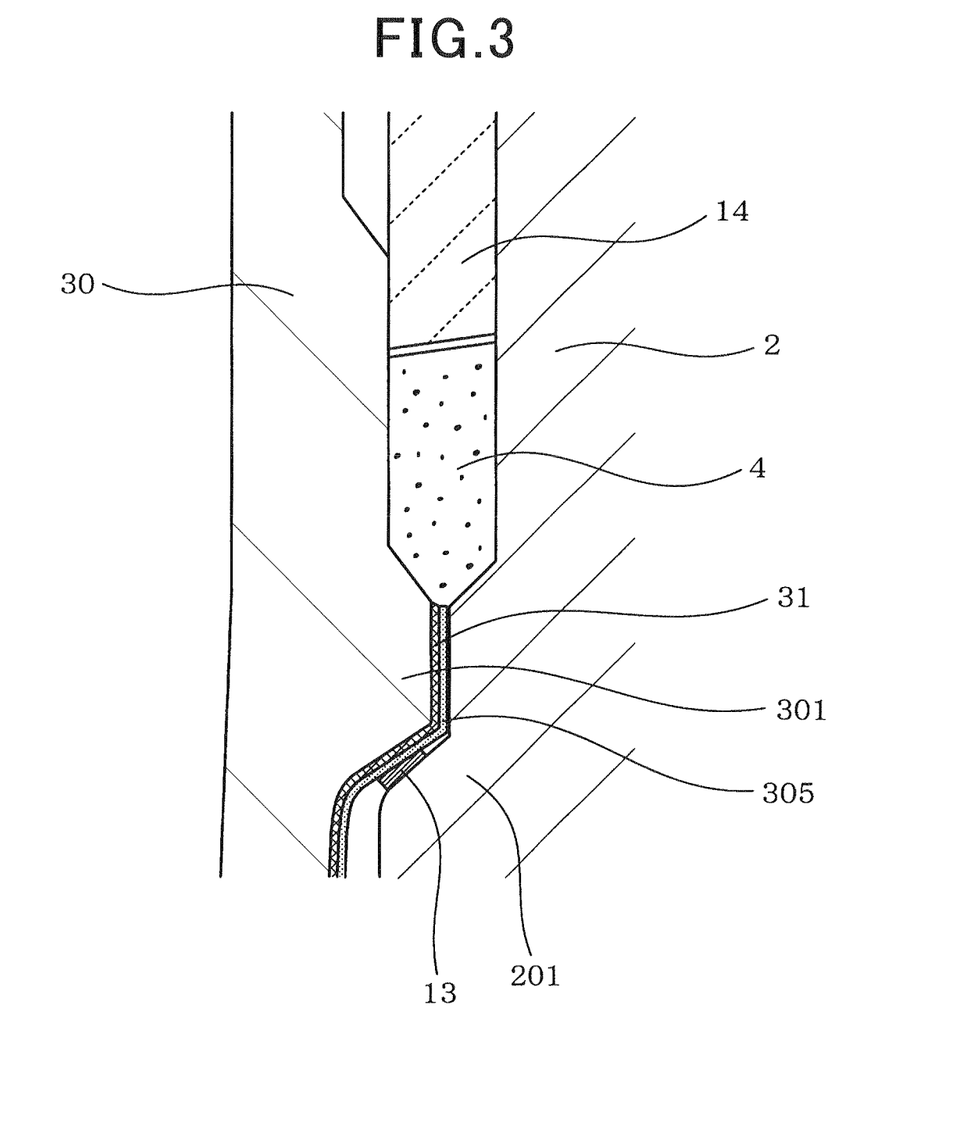
FIG. 3 is an explanation view showing a partial cross section of a filler portion in the gas sensor according to the first exemplary embodiment of the present invention.

FIG. 3 is an explanation view showing a partial cross section of the filler portion 4 in the gas sensor 1 according to the first exemplary embodiment.

As shown in FIG. 3, a diffusion resistance layer and an electrode protection layer 305, etc., are formed so as to cover the outside electrode 301 formed in the solid electrolyte 30.

As shown in FIG. 1 to FIG. 3, an extrusion portion 301 is formed on the outside surface of the solid electrolyte 30 of the gas sensor element 3. The extrusion portion 301 is extruded from the inside surface of the cylindrical housing case 2 toward a diameter direction of the cylindrical housing case 2. The extrusion portion 301 is supported by a reception portion 201 which is extruded from the inside surface of the cylindrical housing case 2 toward the radial inside direction.

A metal packing 13 is arranged between the front end of the extrusion portion 301 and the reception portion 201.

The filler portion 4 and an insulation member 15 made of glass are arranged at the base end of the extrusion portion 301. As previously explained, the filler portion 4 is filled with filler powder. The end surface of the base end of the insulation member 15 made of glass is caulked by the end part 202 at the base end of the cylindrical housing case 2 by a metal ring 161 for use in caulking.

Metal fittings 312 are arranged in the inside of the atmosphere cover 12. Through the metal fittings 312, terminals 311 connected to the gas sensor element 3 are electrically connected to lead wires 313 through the metal fittings 312. The lead wires 313 are connected to terminals of an outside device (not shown) of the gas sensor 1. As shown in FIG. 1, reference number 321 designates an atmosphere insulation member, reference number 322 denotes an elastic insulation member, and reference number 39 indicates a heater.

The filler portion 4 is formed between the cylindrical housing case 2 and the gas sensor element 3 in the gas sensor 1 according to the first exemplary embodiment. The filler portion 4 is filled with filler powder composed of talc which is the principal ingredient thereof. In the structure of the gas sensor 1 according to the first exemplary embodiment, the filler portion 4 is filled with filler powder under a different condition which will be explained below with reference to Table 1 and Table 2.

A description will now be given of the method of manufacturing the filler portion 4 in the gas sensor 1 according to the first exemplary embodiment.

In the method of manufacturing the gas sensor 1 according to the first exemplary embodiment, the filler portion 4 is formed between the cylindrical housing case 2 and the gas sensor element 3 by the following method.

First of all, the metal packing 13 and the gas sensor element 3 are inserted in the inside of the cylindrical housing case 2. Filler powder composed of talc is molded to make a ring shape by using a press molding machine, etc.

After the above steps, the molded filler powder of a ring shape is inserted into the inside of the cylindrical housing case 2. The molded filler powder in the housing tool is pressed with a predetermined load so as to condense the filler powder of a ring shape. Both the insulation member 15 made of glass and the metal ring 161 are inserted into the cylindrical housing case 2. The cylindrical housing case 2 is caulked at the end part 202 of the base end of the cylindrical housing case 2, as shown in FIG. 2.

In a more concrete example, natural talc ore is pulverized by a pulverizing machine (not shown) in order to produce talc raw powder. The talc powder of a predetermined particle size is produced by using an air sifter (or an air classifier), as shown in FIG. 4A.

Because talc is a natural mineral, it contains impurity materials in general. As a result, it is preferable to heat such natural mineral of talc at a temperature of not less than a use temperature of the gas sensor 1. Specifically, natural mineral of talc is heated at a predetermined temperature (which is within a range of 600 to 860° C.), which is not less than a temperature of the filler portion 4 of filler powder of talc. This process is a thermal treatment of talc. It is also possible to execute such a thermal treatment after executing a molding of the filler powder into a ring shape.

As shown in the following Table 1 and Table 2, it is possible to produce the talc powder having an average particle size.

When talc powder having an average particle size of less than 100 μm is used, granulated talc 90 is produced in order to improve the working efficiency, as shown in FIG. 7A.

It is possible to use Chinese talc such as Gaozhou talc which contains impurities such as magnesite of approximately 0.3 to 0.5 wt %, mined in Gaozhou in China. It is also possible to use Haicheng talc (Chinese talc) which is mined in Haicheng in China and contains impurities such as magnesite and dolomite of approximately 0.3 to 0.5 wt %.

Next, it is necessary to add water to the filler powder, water of a predetermined amount is added to talc powder. Table 1 and Table 2 show an added amount of water to the filler powder 100.

When inorganic binder (such as aluminum phosphate) is added to the filler powder, talc powder and inorganic binder are weighed. A predetermined amount of Aluminum phosphate is added to the talc powder, as shown in Table 1 and Table 2.

Next, they are uniformly mixed without destroying talc particles by using a rotary type mixer. Table 1 and Table 2 show an amount of inorganic binder (aluminum phosphate) added to the filler powder of 100 mass % in a case of adding such inorganic binder into the filler powder.

A metal die (not shown) molds a ring shape in the filler powder (such as a "talc ring"). The metal packing 13 and the gas sensor element 3 are inserted in the inside of the cylindrical housing case 2, and the talc ring is fitted between the cylindrical housing case 2 and the gas sensor element 3, as shown in FIG. 1, FIG. 2 and FIG. 3.

The produced talc ring is destroyed by applying a pressure (as a load) of 2 t/cm² along an axial direction of the gas sensor 1 in order to fill the space as the filler portion 4 with the talc 401 (see FIG. 4A and FIG. 4B). As previously described, the filler portion 4 is formed between the cylindrical housing case 2 and the gas sensor element 3.

It is possible to insert the talc ring to the inside of the filler portion 4 by using a metal die and directly pressing the metal die. It is also possible to insert the talc ring by pressing the metal die through the insulation member 15 made of glass.

As shown in FIG. 1 and FIG. 2, after inserting the insulation member 15 made of glass and the metal ring 161, the end portion 202 of the base end of the cylindrical housing case 2 is caulked. This makes the filler portion 4. Although the first exemplary embodiment uses the talc ring having a ring shape, the concept of the present invention is not limited by this. For example, it is acceptable to insert the filler powder into the filler portion 4 as the space or gap formed between the cylindrical housing case 2 and the gas sensor element 3 without using the molded filler powder of a ring shape.

As shown table 1 and Table 2, the first exemplary embodiment prepared thirty four test samples as the gas sensors, each having a different condition of filler powder stored in the filler portion. The first exemplary embodiment used a different particle size of talc, a different amount of water to be added to the filler powder of 100 mass %, a different amount of binder (inorganic binder such as aluminum phosphate) to be added to the filler powder 100 of 100 mass %. In order to measure an average particle size of the filler powder, the first exemplary embodiment used a robot shifter RPS-85C manufactured by SEISHIN ENTERPRISE CO., LTD in JAPAN. Such a robot shifter RPS-85C is a frequency-changeable analyzer which automates all the process of sample input, sieving, weighing, and measurement result calculation.

The first exemplary embodiment detected a degree (%) of c-axis orientation, a porosity (%), a coefficient of thermal expansion (/° C.) of the filler powder of each test sample. Further, the first exemplary embodiment detected a leakage amount of gas which was leaked through the filler portion in each test sample in order to evaluate the airtightness of each test sample.

(Degree of C-Axis Orientation and Coefficient of Thermal Expansion)

The first exemplary embodiment prepared a test sample of the filler powder which was produced under the same condition of producing the filler powder in the filler portion. The prepared test sample of the filler powder was molded into a cuboid of 4×5×50 (mm$^3$) by using a metal die. A load of 2 t/cm$^2$ was then applied onto an area of 5×50 mm$^2$ of the cuboid of the prepared test sample of the filler powder. A coefficient of thermal expansion along a longitudinal direction of the prepared test sample was detected by a contact type thermal expansion meter DL-7000 manufactured by ULVAC-RIKO, Inc. in Japan.

The detection condition was as follows:
Temperature: room temperature to 700° C.; and
Rate of temperature rise: 10° C./min.

FIG. 5 shows the relationship between the degree of c-axis orientation of talc crystal along an axial direction of the gas sensor and the coefficient of thermal expansion of talc. It is possible to calculate a theoretical relationship between the degree of c-axis orientation of talc and the coefficient of thermal expansion of talc. As shown in FIG. 5, when the c-axis of talc is orientated toward an axial direction of the gas sensor, the gas sensor has the minimum coefficient of thermal expansion of the filler powder in the filler portion. The first exemplary embodiment calculated the degree of c-axis orientation of each test sample on the basis of the coefficient of thermal expansion in the relationship shown in FIG. 5. Table 1 and Table 2 show the calculation result of the degree of c-axis orientation of talc in each test sample.

The first exemplary embodiment calculated the degree of c-axis orientation of the molded talc of filler powder. It is also possible to calculate the degree of c-axis orientation of talc by the following method.

Talc is extracted from the filler portion of the test sample as the gas sensor. The coefficient of thermal expansion of the talc is detected. The degree of c-axis orientation of the talc is calculated on the basis of the relationship shown in FIG. 5. In the latter method, the talc is formed in a cuboid shape and the coefficient of thermal expansion of the talc is detected by using a contact type thermal expansion meter DL-7000 under the same conditions of the former method.

The degree of c-axis orientation of the test sample is calculated on the basis of a detected coefficient of thermal expansion (CTE) along a direction which is perpendicular to an axial direction of the test sample as the gas sensor.

(Porosity)

The first exemplary embodiment detected a porosity of each test sample by using an automatic mercury porosimeter AUTO PORE 9520 manufactured by SHIMADZU CORPORATION in Japan.

The automatic mercury porosimeter AUTO PORE 9520 detected the volume of pores in each test sample by using a mercury penetration method (or a mercury press-in method) and a porosity of each test sample was calculated.

Specifically, the cylindrical housing case of each test sample as the gas sensor was cut, and talc (as the molded talc) in the filler portion was extracted from the filler portion. Three grams of mold talc was placed in a measurement cell in the automatic mercury porosimeter AUTO PORE 9520 in order to detect the volume of pores in the mold talc and a porosity of the mold talc. Table 1 and Table 2 show the detection results of the volume of pores and the porosity of the mold talc of each test sample.

(Airtightness)

The first exemplary embodiment detected a leakage amount (cc/min) of air from the filler portion of each test sample.

Specifically, the filler portion in the test sample as the gas sensor was heated and cooled repeatedly. That is, the first exemplary embodiment executed 1000 times a repetition of thermal shock cycle of each test sample. That is, in each of the thermal shock cycle, the first exemplary embodiment heated the filler portion of each test sample to 1000° C., and then cooled the filler portion to the room temperature (approximately 25° C.). After the repetition of thermal shock cycle, air was introduced from the atmosphere introduction side or the exhaust side of each test sample. At this time, the first exemplary embodiment kept a difference in pressure between the atmosphere side and the exhaust side of each test sample as the gas sensor at 400 kPa. The first exemplary embodiment detected a leakage amount of air which was leaked through the exhaust side or the atmosphere side by a mass flow rate detection method. Table 1 and Table 2 show the detection results of each of the test samples.

TABLE 1

| Test sample No. | Porosity (%) | Degree (%) of c-axis orientation | CTE (×10$^{-6}$/° C.) | Average particle size of talc | Added amount of water (mass %) | Added amount of binder (mass %) | Leakage amount of air (cc/min) |
|---|---|---|---|---|---|---|---|
| 1 | 19 | 90 | 4.8 | 20 | — | — | 0.5 |
| 2 | 9.2 | 79 | 6.3 | 100 | — | — | 0.15 |
| 3 | 8 | 73 | 7.3 | 200 | — | — | 0.11 |
| 4 | 7.2 | 70 | 7.7 | 300 | — | — | 0.09 |
| 5 | 7.4 | 64 | 8.2 | 400 | — | — | 0.09 |
| 6 | 8.3 | 60 | 8.7 | 600 | — | — | 0.12 |
| 7 | 14 | 59 | 8.9 | 1000 | — | — | 0.21 |
| 8 | 7.2 | 75 | 6.9 | 200 | 0.1 | — | 0.09 |
| 9 | 7.2 | 79 | 6.3 | 200 | 0.5 | — | 0.08 |
| 10 | 7.1 | 81 | 6.1 | 200 | 1.0 | — | 0.08 |
| 11 | 7 | 83 | 6.0 | 200 | 1.5 | — | 0.08 |
| 12 | 16 | 86 | 5.4 | 200 | 2.0 | — | 0.28 |
| 13 | 7.1 | 70 | 7.7 | 400 | 0.1 | — | 0.07 |
| 14 | 6.9 | 75 | 6.85 | 400 | 0.5 | — | 0.07 |
| 15 | 6.8 | 76 | 6.7 | 400 | 1.0 | — | 0.07 |
| 16 | 6.9 | 77 | 6.6 | 400 | 1.5 | — | 0.08 |
| 17 | 17 | 78 | 6.5 | 400 | 2.0 | — | 0.30 |

TABLE 2

| Test sample No. | Porosity (%) | Degree (%) of c-axis orientation | CTE (×10$^{-6}$/° C.) | Average particle size of talc | Added amount of water (mass %) | Added amount of binder (mass %) | Leakage amount of air (cc/min) |
|---|---|---|---|---|---|---|---|
| 18 | 16 | 90 | 4.7 | 20 | — | 1.0 | 0.45 |
| 19 | 13 | 87 | 5.3 | 100 | — | 1.0 | 0.24 |
| 20 | 11 | 86 | 5.4 | 200 | — | 1.0 | 0.21 |
| 21 | 7.5 | 80 | 6.2 | 300 | — | 1.0 | 0.14 |
| 22 | 6.9 | 77 | 6.6 | 400 | — | 1.0 | 0.10 |
| 23 | 6.5 | 74 | 7.1 | 600 | — | 1.0 | 0.08 |
| 24 | 17 | 63 | 8.3 | 1000 | — | 1.0 | 0.23 |
| 25 | 15 | 87 | 5.2 | 100 | — | 2.0 | 0.30 |
| 26 | 10.5 | 86 | 5.4 | 200 | — | 2.0 | 0.25 |
| 27 | 7.2 | 84 | 5.7 | 300 | — | 2.0 | 0.22 |
| 28 | 6.5 | 82 | 6.0 | 400 | — | 2.0 | 0.19 |
| 29 | 6.2 | 76 | 6.7 | 600 | — | 2.0 | 0.12 |
| 30 | 14 | 64 | 8.2 | 1000 | — | 2.0 | 0.21 |
| 31 | 6.4 | 86 | 5.4 | 400 | — | 3.0 | 0.21 |
| 32 | 6.2 | 77 | 6.6 | 600 | — | 3.0 | 0.13 |
| 33 | 6.5 | 86 | 5.4 | 400 | — | 4.0 | 0.22 |
| 34 | 6.2 | 78 | 6.55 | 600 | — | 4.0 | 0.11 |

It can be understood from the detection results shown in Table 1 and Table 2 that the test samples (for example, the test sample numbers 2 to 6, 8 to 11, 13 to 16, 21 to 23, 27 to 29, 32 and 34) having the degree of c-axis orientation within a range of 60% to 85% and the porosity of not more than 10% have a less amount of gas leakage and a high airtightness.

That is, it is possible for the filler powder such as talc powder, with which the filler portion 4 is filled in the gas sensor 1 according to the first exemplary embodiment, to approach the coefficient of thermal expansion (CTE) of the cylindrical housing case 2 and the gas sensor element 3 when the filler portion 4, namely, the filler powder in the filler portion 4, has the degree of c-axis orientation within the range of 60% to 85% and the porosity of not more than 10% (see FIG. 1 to FIG. 3).

This makes it possible for the filler portion 4 in the gas sensor 1 according to the first exemplary embodiment to not be damaged by a repetition of thermal shock cycle which repeatedly causes expansion and contraction of each of the sensor components such as the cylindrical housing case 2, the gas sensor element 1, etc., in the gas sensor. As a result, this improved feature of the gas sensor 1 makes it possible to better prevent the airtightness of the filler portion 4 from being deteriorated. Even if a force is applied to the gas sensor 1 in a direction which is different from an axial direction of the gas sensor 1, almost no filler powder composed of talc as the principal ingredient thereof in the filler portion 4 moves. This makes it possible to better prevent the airtightness of the filler portion 4 from being deteriorated.

The filler portion 4 in the gas sensor 1 according to the first exemplary embodiment is filled with the compressed powder of natural mineral of talc as the filler powder. As a result, it is possible to approximately completely fill voids or cavity formed in the filler portion 4 with the compressed powder of talc because adjacent layers of talc 401, as layered compound which forms the compressed powder 40, slide relative to each other (see FIG. 4B). Although layers of the talc 401 forming one compressed powder slide in the same direction, but various compressed blocks composed of the layered powder are packed in different direction in the filler portion 4. The different blocks of the compressed powder slide in the same direction and make a plurality of groups of talc. Such a plurality of groups of talc is present in different directions. This makes it possible for the filler powder in the filler portion 4 to easily have the degree of x-axis orientation within the range of 60% to 85%.

It is possible to use compressed powder which is coated with water or inorganic binder. This makes it possible for the talc grains to easily slide relative to each other when the filler portion 4 is filled with the compressed powder of the talc. As a result, it is possible for the filler powder in the filler portion 4 to easily form the degree of c-axis orientation within the range of 60% to 85% and the porosity of not more than 10%.

The gas sensor element 3 has the solid electrolyte made of zirconia. The cylindrical housing case 2 is made of stainless steel such as Steel Use Stainless (SUS as Japanese Industrial Standards). As a result, it is possible for the filler portion 4 to easily handle a repetition of thermal shock cycle which repeatedly causes expansion and contraction of each of components such as the cylindrical housing case 2, the gas sensor element 3, etc., as the sensor components of the gas sensor 1. This makes it possible to better prevent the airtightness of the filler portion 4 in the gas sensor 1 from being decreased.

Second Exemplary Embodiment

A description will be given of a gas sensor 5 according to a second exemplary embodiment of the present invention with reference to FIG. 6.

Figure 6:
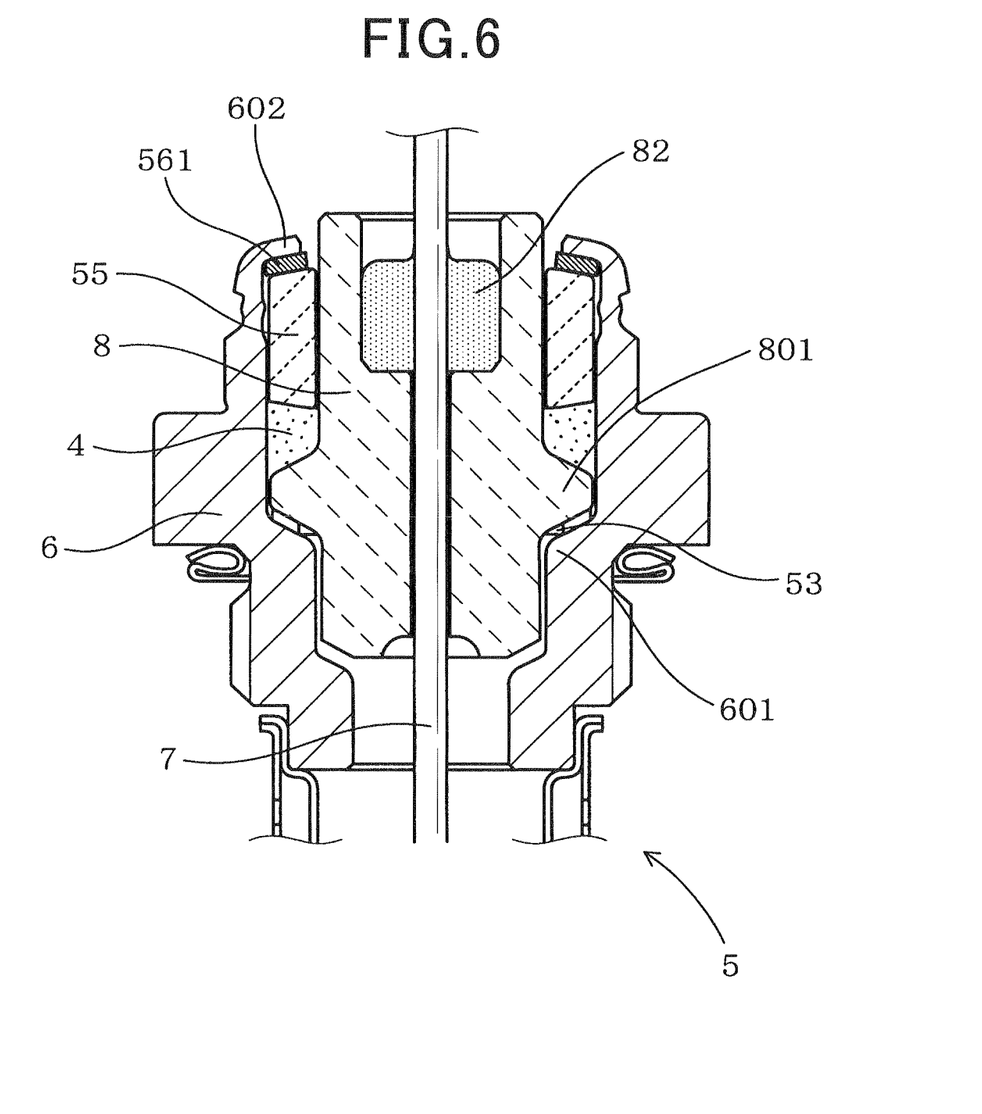
FIG. 6 is an explanation view showing a portion around a cylindrical housing case in a gas sensor according to a second exemplary embodiment of the present invention.

FIG. 6 is an explanation view showing a portion around a cylindrical housing case in the gas sensor 5 according to the second exemplary embodiment. The second exemplary embodiment shows the gas sensor 5 of a lamination type.

As shown in FIG. 6, the gas sensor 5 according to the second exemplary embodiment has a cylindrical housing case 6, a gas sensor element 7 and the filler portion 4.

The gas sensor element 7 is installed in the inside of the cylindrical housing case 6. The filler portion 4 is formed between the inner surface of the cylindrical housing case 6 and the outer surface of a sensor component member 8 of the gas sensor 5. The filler portion 4 is filled with filler powder composed of talc as a layered compound. That is, a space or a gap between the inner surface of the cylindrical housing case 6 and the outer surface of the sensor component member 8 is filled with such talc composed of layered compound. The space is sealed with the filler powder stored in the filler portion 4. The second exemplary embodiment uses an insulator 8 as one of the sensor components of the gas sensor 5. That is, the filler portion 4 is formed between the cylindrical housing case 6 and the insulator 8 in the gas sensor 5.

In the structure of the gas sensor 5 according to the second exemplary embodiment, the gas sensor element 7 of a lamination type is inserted in the inside of the insulator 8. The insulator 8 with the gas sensor element 7 is inserted into and fixed to the cylindrical housing case 6.

In particular, the gas sensor element 7 is a lamination type gas sensor element in which a plurality of ceramics sheets is laminated. The gas sensor element 7 has a rod shaped plate.

The insulator 8 is made of alumina having a coefficient of thermal expansion (CTE) of $8\times10^{-6}/°$ C. The base end of a support portion of the gas sensor element 7 is sealed with glass 82 shown in FIG. 6.

The insulator 8 is inserted into and fixed to the inside of the cylindrical housing case 6 which has a coefficient of thermal expansion (CTE) of $11.5\times10^{-6}/°$ C.

An extrusion portion 801 is fitted to the outside surface of the insulator 8. The extrusion portion 801 extrudes toward an outer radius direction and is supported by a reception portion 601 which is extruded from the inside surface of the cylindrical housing case 6 toward an inner radial direction.

A metal packing 53 is arranged between the front end of the extrusion portion 801 and the reception portion 601.

The filler portion 4 and an insulation member 55 made of glass are arranged at the base end of the extrusion portion 801. As previously explained, the filler portion 4 is filled with filler powder. The end surface of the base end of the insulation member 55 made of glass is caulked by the end part 602 at the base end of the cylindrical housing case 6 by a metal ring 561 for use in caulking.

Like the structure of the filler portion 4 in the gas sensor 1 according to the first exemplary embodiment, the filler portion 4 is filled with the filler powder, which is formed between the cylindrical housing case 6 and the insulator 8. Other components of the gas sensor 5 according to the second exemplary embodiment are the same of the components of the gas sensor 1 according to the first exemplary embodiment.

As a result, it is possible for the filler powder in the filler portion 4 in the gas sensor 5 equipped with the gas sensor element 7 of a lamination type according to the second exemplary embodiment shown in FIG. 6 to approach the coefficient of thermal expansion (CTE) of the cylindrical housing case 6 and the insulator 8 when the filler portion 4, more specifically, the filler powder in the filler portion 4, has the degree of c-axis orientation within the range of 60% to 85% and the porosity of not more than 10% (like the gas sensor 1 according to the first exemplary embodiment).

This makes it possible for the filler portion 4 in the gas sensor 5 according to the second exemplary embodiment to handle a repetition of thermal shock cycle which repeatedly causes expansion and contraction of each of the sensor components such as the cylindrical housing case 6, the insulator 8, etc., in the gas sensor. As a result, this improved feature of the gas sensor 5 makes it possible to better prevent the airtightness of the filler portion 4 from being deteriorated. Even if a force is applied to the gas sensor 5 in a direction which is different from an axial direction of the gas sensor 5, almost no filler powder moves, which is composed of talc as the principal ingredient thereof in the filler portion 4. This makes it possible to better prevent the airtightness of the filler portion 4 from being deteriorated.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A gas sensor comprising:
a cylindrical housing case;
a gas sensor element disposed and fixed to the inside of the cylindrical housing case; and
a filler portion formed between the inner surface of the cylindrical housing case and the outer surface of a sensor component installed in the inside of the gas sensor, the filler portion being filled with filler powder containing talc as a layered compound, and the filler portion formed between the cylindrical housing case and the sensor component being completely sealed with the filler powder,
wherein the talc of the filler powder has an average particle size within a range from not less than 100 μm to less than 400 μm, and a degree of c-axis orientation within a range of 60% to 85%, and a porosity of the filler portion is not more than 10%, and
wherein the filler powder contains water within a range from not less than 0.1 mass % to not more than 1.5 mass % when the filler powder is 100 mass %.

2. The gas sensor according to claim 1, wherein the gas sensor element is a sensor component of the gas sensor, and the filler portion is formed between the cylindrical housing case and the gas sensor element.

3. The gas sensor according to claim 1, further comprising an insulator, wherein the insulator is installed in the inside of the cylindrical housing case, and the gas sensor element is installed in the inside of the insulator, the insulator is the sensor component of the gas sensor, and the filler portion is formed between the cylindrical housing case and the insulator.

4. The gas sensor according to claim 3, wherein the insulator is made of alumina.

5. The gas sensor according to claim 1, wherein the filler portion is filled with the filler powder which is compressed powder of natural mineral of talc.

6. The gas sensor according to claim 1, wherein the gas sensor element has a solid electrolyte made of one selected from zirconia and partially stabilized zirconia, and the cylindrical housing case is made of stainless steel.

7. The gas sensor according to claim 2, wherein the filler portion is formed at a part between the cylindrical housing case and the gas sensor element.

8. The gas sensor according to claim 3, wherein the filler portion is formed at a part between the cylindrical housing case and the insulator.

* * * * *